(12) United States Patent
Nordstrom et al.

(10) Patent No.: US 6,427,082 B1
(45) Date of Patent: Jul. 30, 2002

(54) OPTICAL METHODS AND SYSTEMS FOR RAPID SCREENING OF THE CERVIX

(75) Inventors: Robert Nordstrom, Hanover; Mark Modell, Natick, both of MA (US)

(73) Assignee: MediSpectra, Incorporated, Lexington, MA (US)

(*) Notice: Subject to any disclaimer, the term of this patent is extended or adjusted under 35 U.S.C. 154(b) by 0 days.

(21) Appl. No.: 09/471,700

(22) Filed: Dec. 23, 1999

Related U.S. Application Data

(60) Provisional application No. 60/113,624, filed on Dec. 23, 1998.

(51) Int. Cl.[7] ............................................. A61B 6/00
(52) U.S. Cl. .................... 600/476; 250/461.2; 356/300; 356/342
(58) Field of Search ............................. 600/310, 407, 600/476, 477, 342; 606/2, 3; 356/300, 302, 928, 342; 250/461.1, 461.2

(56) References Cited

U.S. PATENT DOCUMENTS

| | | | | |
|---|---|---|---|---|
| 4,891,829 A | * | 1/1990 | Deckmam et al. | |
| 4,945,478 A | * | 7/1990 | Merickel et al. | |
| 5,003,979 A | * | 4/1991 | Merickel et al. | |
| 5,596,992 A | * | 1/1997 | Haaland et al. | |
| 5,713,364 A | * | 2/1998 | DeBaryshe et al. | |
| 5,768,333 A | * | 6/1998 | Abdel-Mottaleb | |
| 6,119,031 A | * | 9/2000 | Crowley | |
| 6,146,897 A | * | 11/2000 | Cohenford et al. | |
| 6,169,817 B1 | * | 1/2001 | Parker et al. | |

* cited by examiner

*Primary Examiner*—Marvin M. Lateef
*Assistant Examiner*—Runa Shah Qaderi
(74) *Attorney, Agent, or Firm*—Testa, Hurwitz & Thibeault, LLP

(57) ABSTRACT

A method and a system is provided for discriminating between healthy cervical tissue and pathologic cervical tissue based on the fluorescence response of the tissue to laser excitation (LIF) and the backscatter response to illumination by white light (in the spectral range of 360 to 750 nm). Combining LIF and white light responses, as well as evaluating a spatial correlation between proximate cervical tissue sites in conjunction with a statistically significant "distance" algorithm, such as the Mahalanobis distance between data sets, can improve the discrimination between normal and abnormal tissue. The results may be displayed in the form of a map of the cervix representing the suspected pathology.

15 Claims, 12 Drawing Sheets

Figure 9: Rendering of the cervix with a display of the interrogation points.

OPTICAL METHODS AND SYSTEMS FOR RAPID SCREENING OF THE CERVIX

REFERENCE TO RELATED APPLICATIONS:

This application claims priority to provisional patent application No. 60/113,624 filed Dec. 23, 1998.

FIELD OF THE INVENTION

The present invention relates to optical devices and methods for screening of cervical tissue abnormalities.

BACKGROUND OF THE INVENTION

Early detection of a variety of pathologies has been shown to dramatically improve the therapeutic outcome for such pathologies. This is particularly true with cancer, and specifically with cancer of the cervix. In the case of cancer of the cervix and other cervix anomalies, the pap smear test has been used for many years as a screening method for the detection of pre-cancerous conditions as well as for the detection of cancer. Unfortunately, this method suffers from excessive errors and results in too many false positive as well as false negative determinations, which increases the overall cost to the health care system. The method requires the physician to scrape cells from the surface of the cervix and transfer the cells to a laboratory where a cytopathologist examines them under a microscope. Statistics on the false positive readings of pap smears range as high as 30% and false negative error rate of 20% to 30% associated with insufficient cell readings or inexpert readings of pap smears are normal as well.

In the case of false negative determinations, additional colposcopic examinations and biopsies of the cervix are carried out on patients with normal tissue, overloading the health care system unnecessarily. On the other hand, false negative pap smears allow the pathologies to evolve to full cancers that could have been treated earlier at much lower costs and with better outcomes.

Fluorescence spectroscopy, which is capable of distinguishing histologically normal and histologically abnormal tissue, has been used for the detection of cervical neoplasia by comparing fluorescence of a suspicious area of the cervix with normal tissue. Since the location of abnormal tissue is often difficult to determine by eye, this approach tends to require highly trained practitioners to determine normal tissue.

In other tissues types, pre-cancerous conditions present themselves in ways that make identification of potential abnormal sites over normal sites much easier than in the cervix. In the colon, for example, the presentation of polyps forming on the interior wall is an indication of possible malignant growth. Spectroscopic studies comparing tissue responses of polyp regions from non-polyp regions show a high degree of difference in the optical signatures of the tissue. This is to be expected, considering the morphologic differences in the tissues. In the cervix, however, surface changes caused by the presence of lesions are often difficult, if not impossible, to see. This indicates that the tissue differences between normal and abnormal tissue are often very subtle, and optical techniques must attempt to distinguish these subtle features.

The tissue fluorescence may be excited, for example, by excitation with UV light. Other spectroscopic methods employ multiple fluorescence excitation wavelengths and use discrimination functions, which frequently cannot easily classify the health of the tissue, even when comparing spectra from the same cervix. Accordingly, these spectroscopic methods have little predictive power when used with other cervixes since each "standard" (normal tissue) invariably may have to be determined for each cervix screened.

It would therefore be desirable to provide a screening system and method that provide an immediate indication of the health of the cervical tissue and could replace a pap smear test as a screening modality, is simpler to perform, does not depend on the specific cervix screened, and can be administered by personnel having minimal medical training.

SUMMARY OF THE INVENTION

The invention is directed to provide a system and a method of optically classifying cervical tissue into pathological classes, without a priori knowledge if a tissue and/or which tissue may or may not be normal. The classification is based on a statistical algorithm which associates the tissue with the respective tissue classes by computing a "distance" between a tissue response and a training (reference) response. The tissue is assigned to the pathological class which produces the smallest distance.

According to one aspect of the invention, a source of optical radiation is provided which induces at least one of a fluorescence and backscatter response in the cervical tissue. A detector detects the response induced in the cervical tissue and produces a response signal. A processor compares the response signal with reference signals obtained from cervical tissue samples of known pathology by computing a distance between the response signal and the reference signals. The reference signals are grouped into at least two pathological classes and the cervical tissue producing the response signal is assigned to the class which produces the smallest distance.

According to another aspect of the invention, a diagnostic system produces a map of the cervix according to pathological classes. A source of optical radiation induces at least one of a fluorescence and backscatter response in cervical tissue, wherein the source is scanned in a predetermined pattern over tissue sites of at least a portion of the cervix. A detector detects the response induced in the cervical tissue and produces a response signal. A processor compares the response signal with reference signals obtained from cervical tissue samples of known pathology by computing a distance between the response signal and the reference signals from the different tissue sites. The reference signals are grouped into at least two pathological classes and the cervical tissue which produces the response signal at the different tissue sites is assigned to the class which produces the smallest distance for that site. The assigned classes for the different tissue sites can be rendered to produce the map of the cervix.

According to yet another aspect of the invention, a method is provided of optically classifying cervical tissue into pathological classes, which includes exciting the cervical tissue with optical radiation and inducing at least one of a fluorescence and backscatter response in the cervical tissue, detecting the response induced in the cervical tissue and producing a response signal, comparing the response signal with reference signals which are obtained from cervical tissue samples of known pathology and grouped into at least two pathological classes, computing a distance between the response signal and the reference signals, and assigning the cervical tissue to the class which produces the response signal having the smallest distance.

According to still another aspect of the invention, a method is provided of optically classifying cervical tissue into pathological classes, which includes exciting the cervical tissue with optical radiation and detecting a fluorescence response in the cervical tissue, comparing the fluorescence response with a fluorescence reference response which were obtained from cervical tissue samples of known pathology and grouped into at least two pathological classes, by computing a first distance between the fluorescence response and the reference response and assigning the cervical tissue to the class which produces the response signal having the smallest first distance. The method further includes detecting a backscatter response from the cervical tissue at the same location in the cervix, comparing the backscatter response with a backscatter reference response which were obtained from cervical tissue samples of known pathology and grouped into the at least two pathological classes, by computing a second distance between the backscatter response and the backscatter reference response and assigning the cervical tissue to the class which produces the backscatter response signal having the smallest second distance. If the class of the cervical tissue based on the first distance is identical to the class of the cervical tissue based on the second distance, then the cervical tissue is classified into the class representing both the first and second distance. On the other hand, if the class of the cervical tissue based on the first distance is different from the class of the cervical tissue based on the second distance, then the fluorescence response is combined with the backscatter response and a third distance between the combined response and a respective combined fluorescence and backscatter reference response is computed. The cervical tissue is assigned to the class which produces the combined response signal having the smallest third distance.

Embodiments of the invention may include one or more of the following features. The computed distance may be a Mahalanobis distance, which may be computed by including Quadratic Discriminant Analysis (QDA) and/or Regularized Discriminant Analysis (RDA) to eliminate problems caused by singularities. The source of the optical radiation, which may be the cervical probe, and/or the detector may be placed so as not to contact the cervical tissue. The at least two pathological classes may include CIN (cervical intraepithelial neoplasia) and NED (squamus normal or no evidence of disease) tissue. The source of optical radiation may be an ultraviolet (UV) source, such as a UV laser, for example, a frequency-tripled Nd:YAG laser, a nitrogen laser or a He-Cd laser, emitting at a wavelength between 300 and 400 nm. Alternatively or in addition, the source of optical radiation is a broadband light source emitting in the visible/infrared spectral range, such as a xenon lamp. the detector may includes at least two detection systems, with a first system detecting the fluorescence response and a second system detecting the backscatter response. The response signal may be a normalized signal obtained, for example, by scaling the fluorescence response and/or the backscatter response with respect to the other of the backscatter response and/or fluorescence response. The backscatter response may be calibrated against a target having a known spectral reflectivity, for example, a reflectivity of approximately 10%. The reference signals may be stored in a memory.

Further features and advantages of the present invention will be apparent from the following description of certain preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF CERTAIN PREFERRED EMBODIMENTS

Figure 1:
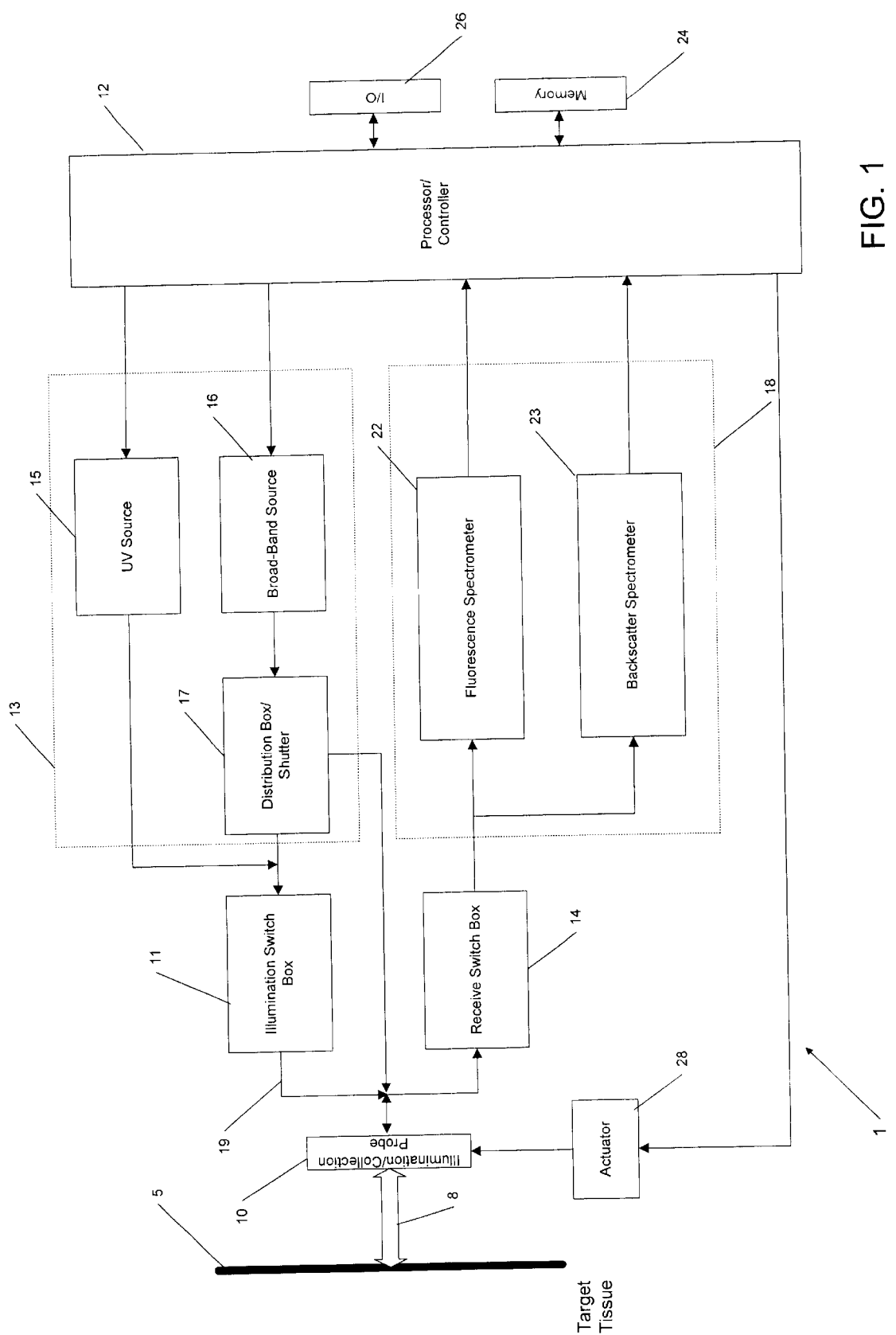
FIG. 1 is a block diagram of a typical screening probe.

The present invention comprises systems and methods of using algorithms on optical responses of cervical tissue obtained from target tissues in subject population to be screened. The data are taken from a plurality of different sites within the target tissue, typically at least 100 such sites covering the region of interest in the tissue are probed. The optical response consists of fluorescence from the tissue induced by illumination with ultraviolet (UV) light and/or backscattering of white light from substantially the same tissue sites.

By way of background information, spectra are taken from the screened tissue, each from a different point in a given cervix. An algorithm, which classifies the detected spectra as either NED (No Evidence of Disease) or CIN (Cervical Intraepithelial Neoplasia), is applied to each of these spectra. Pathologists classify CIN into the three subgroups: CIN I, CIN II, and CIN III, depending of the stage or grade of the CIN. In addition, intermediate classifications between these subgroups may be used. These are the CIN I/II transition, and the CIN II/III class.

Tissue of class CIN I most often does not progress toward a cancerous condition. It is estimated that only about 10% to 20% of the identified CIN I tissue progresses to the stage of CIN II/III. For the most part, the CIN I regresses to normal tissue over time. Additionally, about 20% of the CIN II/III lesions progress to carcinoma in situ (CIS). However, the presence of lesions of type CIN II/III will most likely prompt the physician to perform a biopsy of the site.

With a conventional screening mode, such as the pap smear, the location of the CIN II/III lesion (or lesions) is not known. The cluster of cells exfoliated from the surface of the cervix by the scraping paddle is studied by the cytopathologist without knowledge of the location of origin of the cells on the cervix. The presence of a high-grade disease such as CIN II/III may be indicated by as few as ten to twenty cells on a microscope slide of several millions of cells.

Optical devices used for cervical screening should also be capable of differentiating between normal tissue (NED and metaplastic) and abnormal tissue (referring to the various CIN categories discussed above), and between the different categories of CIN. The determination whether a cervix is positive (i.e. diseased) or negative (i.e. free from disease) is a question of judgment and accepted medical practice. In some cases, the presence of any CIN grade classification within all the spectral responses will classify that cervix as "positive", while in other cases, CIN I would be classified as negative. Of course, all NED results are classified as "negative" in the screening procedure.

Sensitivity of the optical measurement is defined as the ability to find disease when disease is present. Therefore, sensitivity is measured by dividing the number of patients who are diagnosed as having the disease, by the total number of patients who actually have the disease, as determined by pathological examination. A sensitivity value close to unity for a diagnostic device indicates that the device has the ability to identify patients with disease. However, the sensitivity value does not indicate the number of patients who were also identified as having the disease, but are actually disease-free. For this, the device specificity must also be indicated. Specificity is defined as the ratio of those patients who were diagnosed as being free from the disease, divided by the total patient number without the disease. A high value of specificity (approaching unity) indicates that patients do not have to go to the next level of treatment, unless medically indicated.

FIG. 1 shows a block diagram of an optical screening system 1 which includes, among others, an optical probe 10, an optical illumination unit 13, an optical response detection unit 18 and a processor/controller 12. The optical illumination unit 13 includes an optical excitation source 15, such as a UV laser source which may be a nitrogen laser emitting at 337 nm or a frequency-tripled Nd:YAG laser emitting at 355 nm, and a broadband "white" light source 16, for example, a xenon lamp. Other light sources known in the art may also be employed.

An illumination switch box 17 can be used to redirect the light resources 15, 16 to provide either UV excitation or backscatter illumination 8 of specific points on the target cervix. In addition, light for the broadband light source 16 can also be redirected by a distribution box 17 to provide general illumination of the cervical tissue to locate the optical probe 10 in proper proximity to the tissue 5 with the help of, for example, a video camera (not shown). The best time to locate the probe 10 is when optical fluorescence or backscatter responses are not elicited from the target tissue, for example, just prior to or between measurements.

The optical probe 10 may be formed of an optical fiber path 19 consisting, for example, of a multiple-fiber bundle which is connected to the illumination switch box 11 and terminates in a multiple-fiber tip, thereby eliminating moving parts. The magnification in the illumination optics may be adjustable so that the final image of the fiber arrangement matches the required coverage on the surface of the cervix. Each fiber may be illuminated separately, for example, by using an optical switching or scanning arrangement located in the switch box 11 and controlled by the processor/controller 12, effectively scanning the illuminating point over the surface to obtain optical responses from a large number of tissue sites. The illuminating light may be scanned in a two-dimensional raster pattern, as a helical pattern and/or any other pattern wherein the cervical sites are illuminated in a predetermined order and detected.

Multiple points on the cervix can be illuminated simultaneously to reduce the time for a complete scan. These points should be well spaced to prevent "cross talk" among the receiver channels and assure that responses are well assigned to the specific spot. To cover a larger number of such points, the transmit switch box illuminates multiple fiber ends simultaneously using the laser light (for fluorescence measurements) or the lamp (for elastic backscatter measurements). By stepping through the illumination pattern in a predetermined order, responses from a larger number of points can be generated than with uniform illumination from a single source.

The tissue response, i.e. fluorescence and/or backscattered light response, is transmitted back to a response detection unit 18, for example, through the fiber-optic bundle 19. A "Receive Switch Box" 14 may be employed to redirect and distribute the tissue response to one or more spectrometers. For example, the laser-induced fluorescence (LIF) signal which is typically the weaker signal, may be coupled to a spectrometer 22 having, for example, an ICCD (Intensified CCD) camera (not shown), whereas the stronger backscattered light response may be coupled to a spectrometer 23 coupled, for example, to a CCD camera (not shown).

It will be understood that the spectrometer 23 can be eliminated from the system if only LIF measurements are taken. Conversely, the spectrometer 22 can be eliminated if only a white light source 16 is used for tissue illumination. Likewise, the distribution box 17 in the illumination unit 13 may be eliminated if the white light source is used only for general video illumination and not for spectroscopic purposes. However, the white light source may still be timed to illuminate the target tissue between measurements of the fluorescence responses, since continuous white light illumination during the LIF measurement may mask the fluorescence responses.

Timing functions and control as well as data processing and presentation of screening algorithm results are handled in the processor/controller 12, which may include control functions, such as actuating selected fibers of fiber arrangement 19, timing functions, such as controlling the switch boxes 11, 14 and the distribution box 17, and data processing functions, such as writing to and reading from memory 24 and communicating with input/output (I/O) devices 26. The I/O devices 26 may include keyboards, pointing devices, network interfaces, monitors and printers and may be interfaced with the processor/controller 12. I/O devices of this type are known in the art and are therefore not shown in detail in FIG. 1. The printers may also include film printers. The memory 24 may include random-access memory (RAM), conventional computer data storage devices, such as floppy and hard disks, magnetic tape and the like, which may be removable, for storing, for example, calibration parameters (training sets) and screening algorithms. The processor/controller 12 may be a general purpose computer, such as a PC, and may also control an actuator 28 used to scan the probe 10 across the cervical tissue to provide a pathological classification map of the cervix.

Figure 2:
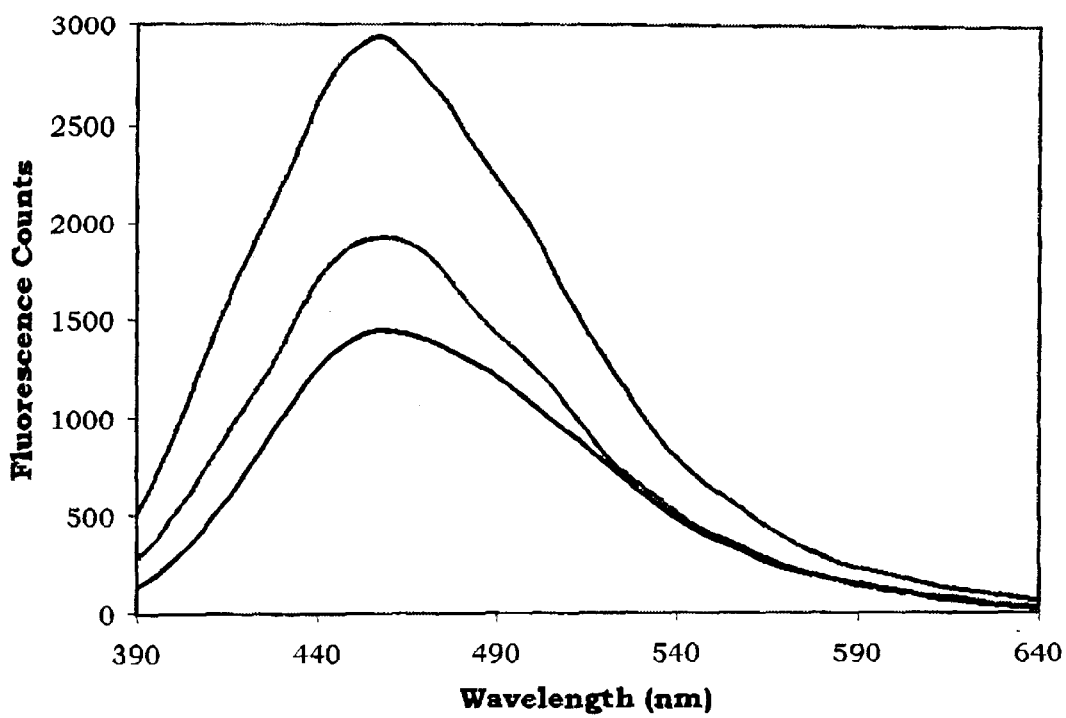
FIG. 2 shows a typical fluorescence response spectra to 355 nm excitation of NED tissue samples.

FIG. 2 shows three exemplary LIF spectra probed with a UV laser excitation beam at 355 nm for tissue that was classified as NED by a subsequent pathologic examination of the excised tissue from the same sites on the cervix.

Figure 3:
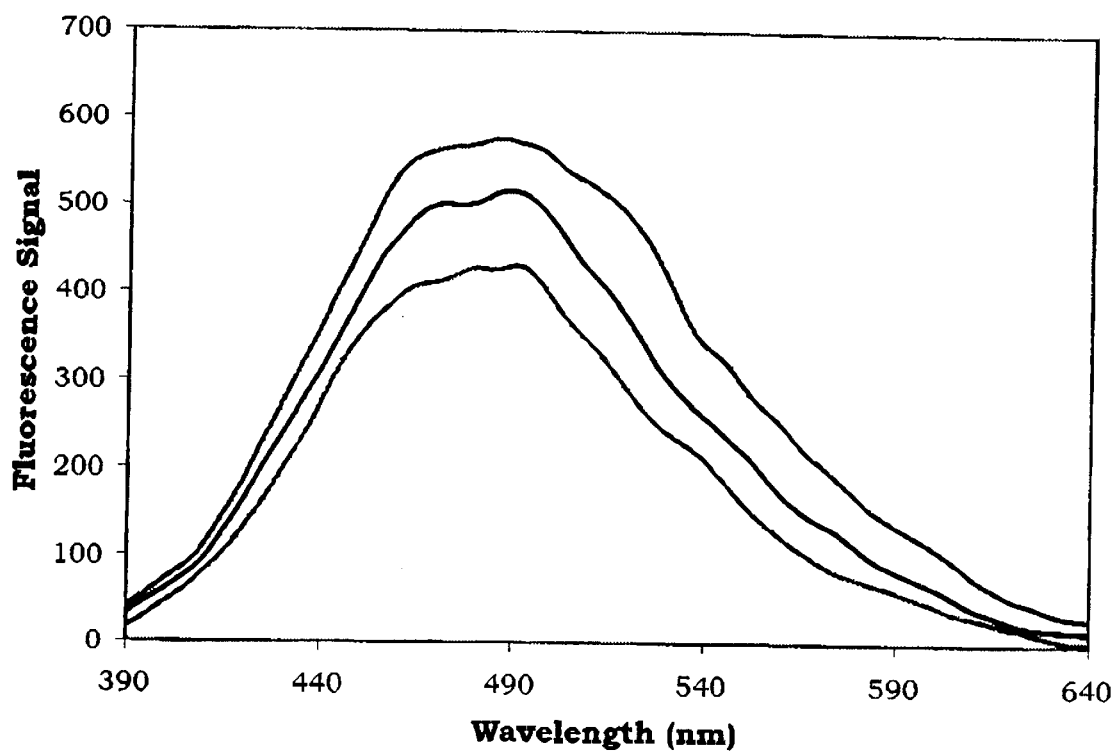
FIG. 3 shows a typical fluorescence response spectra to 355 nm excitation of CIN II–III tissue samples.

FIG. 3 shows three exemplary LIF spectra probed with a UV laser excitation beam at 355 nm for tissue that was classified as CIN II/III by a subsequent pathologic examination of the excised tissue from the same sites on the cervix. The difference between the NED spectra of FIG. 2 and the CIN spectra of FIG. 3 may not be evident to the untrained eye. One feature differentiating the spectra appears to be the wavelength at which the maximum signal occurs.

Figure 4:
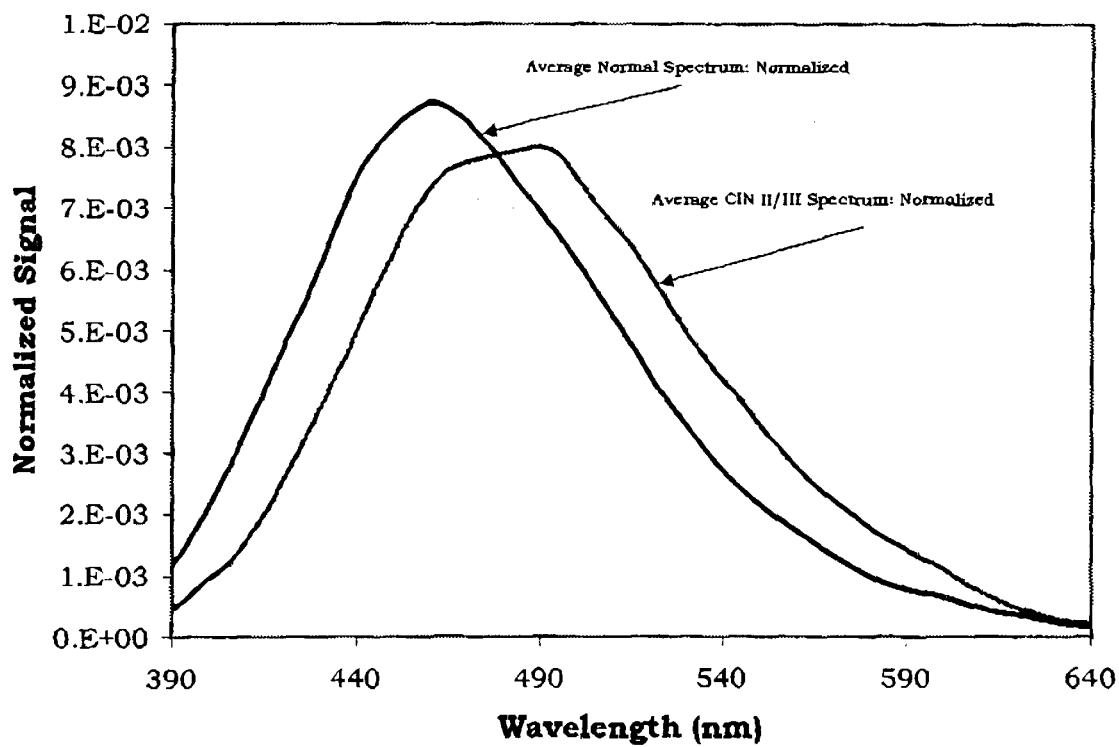
FIG. 4 shows normalized fluorescence response spectra to 355 nm excitation of an NED and a CIN II–III tissue sample, respectively.

Referring now to FIG. 4, an averaged normalized spectrum of the fluorescence response received from a site classified as negative or NED (no evidence of disease) is plotted along with an averaged normalized spectrum obtained from positive tissue samples (CIN II–III, cervical intraepithelial neoplasia of grade II–III). The spectra were probed with a UV laser excitation beam at 355 nm. It was observed that normalizing each fluorescence intensity spectrum received for the points probed on the cervix by dividing each spectrum by the total area under the fluorescence spectrum from 390 nm to 620 nm provides for standardized responses, eliminating overall intensity fluctuations between probed points. As seen in FIG. 4, the maximum of the spectral response of the positive tissue samples is shifted to longer wavelength with respect to the spectral response of the positive tissue samples. This characteristic shift can be used to differentiate between NED and CIN sites.

Figure 5:
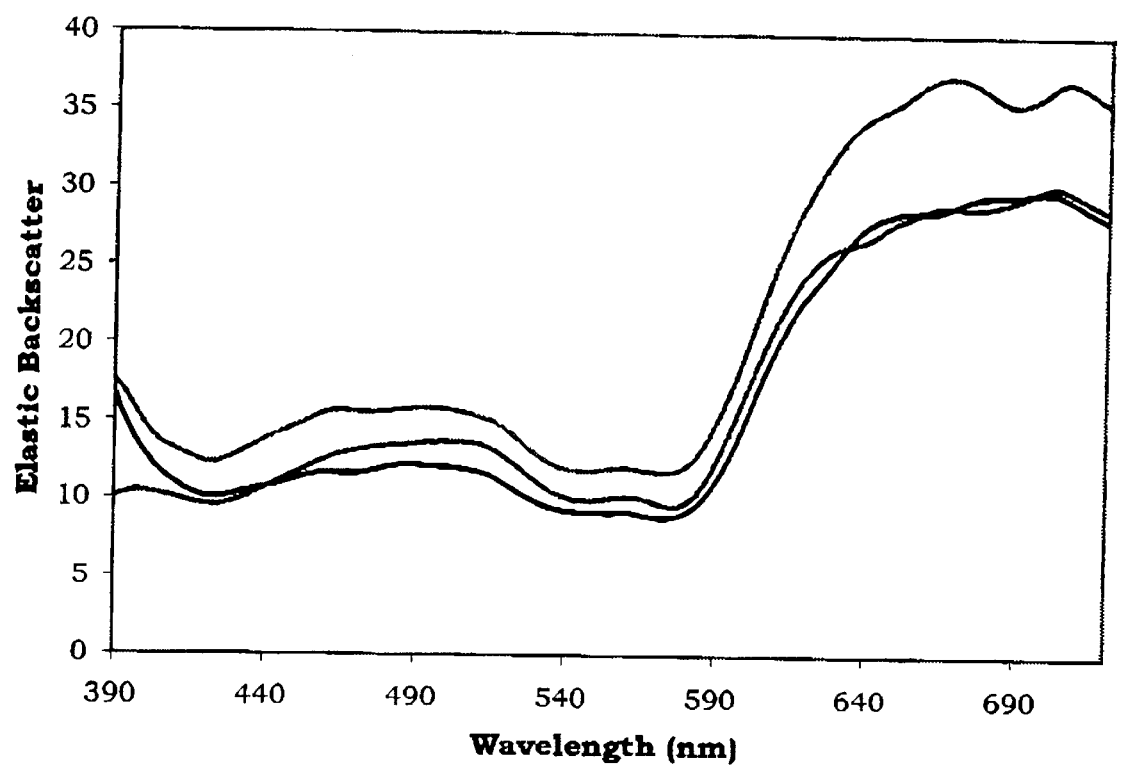
FIG. 5 shows typical white light backscattered spectra from NED tissue samples.

FIG. 5 shows three exemplary raw backscatter spectra probed with white light excitation for tissue that was classified as NED by a subsequent pathologic examination of the excised tissue from the same sites on the cervix. The spectra show a large degree of intensity variation caused by geometrical and physical conditions of the cervical surface and therefore cannot be used for a quantitative discrimination between the two classes. Accordingly, optical responses to white light excitation require normalization as well.

Figure 6:
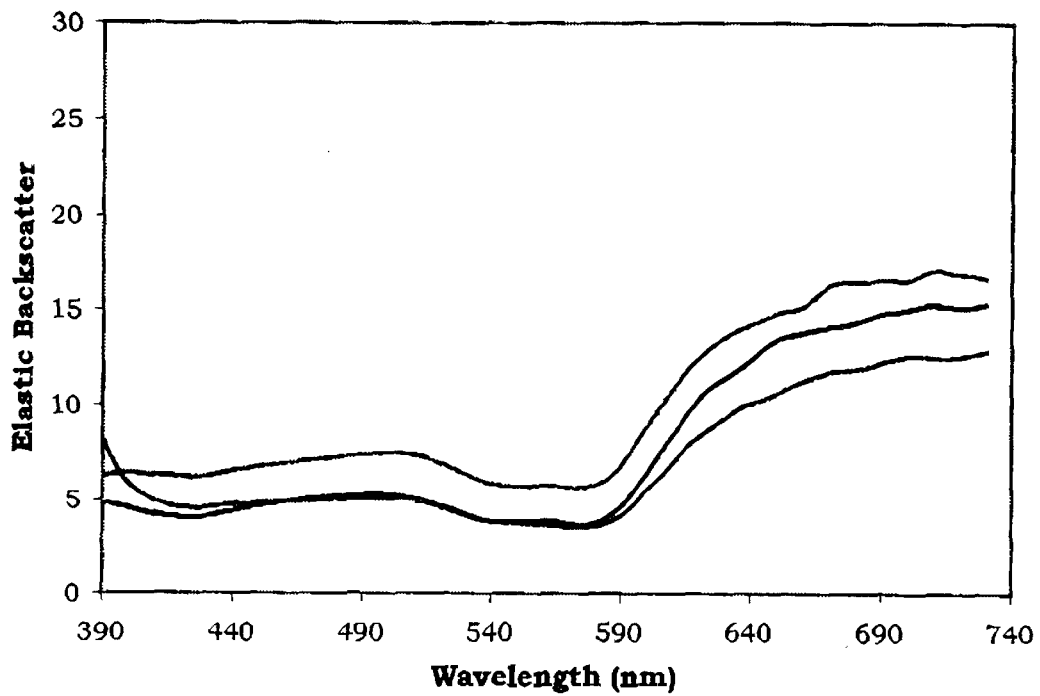
FIG. 6 shows typical white light backscattered spectra from CIN II–III tissue samples.

FIG. 6 shows three exemplary raw backscatter spectra probed with white light excitation for tissue that was classified as NED CIN II/III by a subsequent pathologic examination of the excised tissue from the same sites on the cervix. The difference between the NED spectra of FIG. 5 and the CIN spectra of FIG. 6 may not be evident to the untrained eye. One feature differentiating the spectra appears to be the wavelength at which the various peak signals are observed. Another differentiating feature appears to be the relative amplitudes of the respective peak signals.

Figure 7:
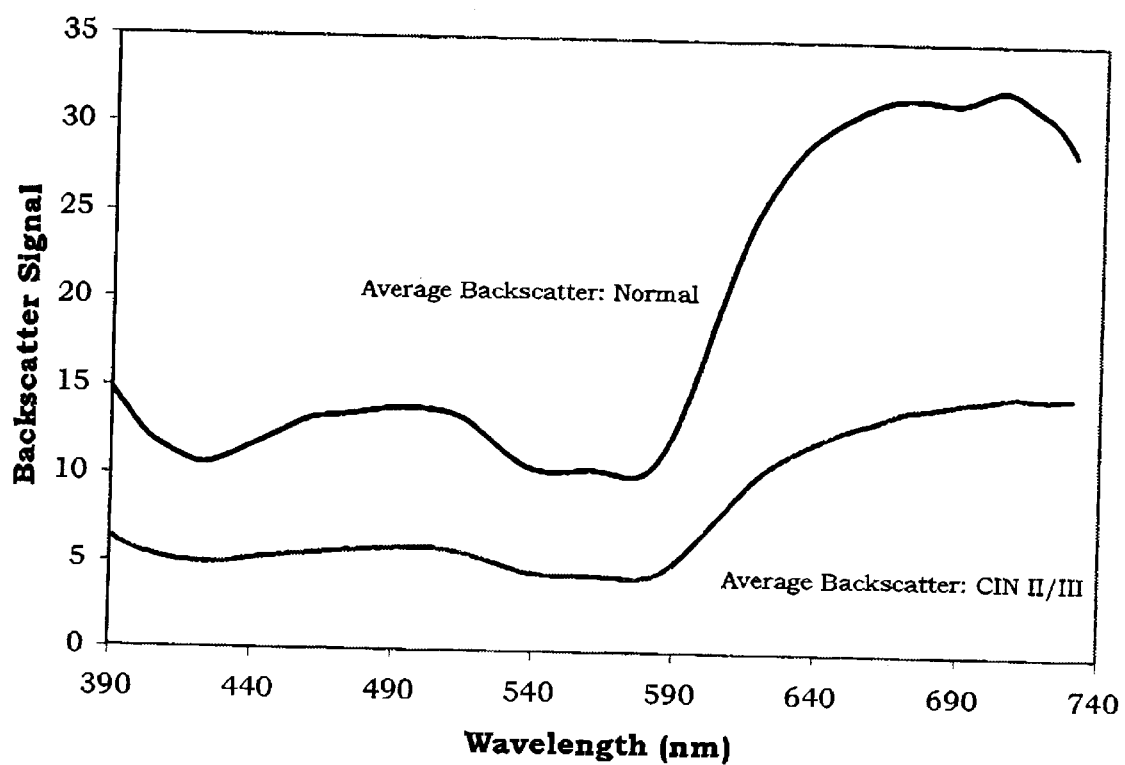
FIG. 7 shows typical normalized white light backscattered spectra averaged from NED tissue samples and CIN II–III tissue samples, respectively.

Referring now to FIG. 7, an averaged normalized spectrum obtained from negative tissue samples (NED) is plotted along with an averaged normalized spectrum obtained from positive tissue samples (CIN II–III). The spectra were probed with white light excitation having the same spectral characteristics. The characteristic features of the spectra can be used to differentiate between NED and CIN sites using the algorithm which will be described in detail below.

As mentioned above, the fluorescence intensity from a sample depends on different geometrical and physical factors which can prevent efficient coupling of the excitation light into cervical tissue. It should be appreciated that the cervix is not a homogeneous tissue of uniform thickness. It has a curved surface and the amount of fluorescence excitation light that enters the tissue is a function of the angle of incidence of the incoming beam. As a result, the absolute fluorescence intensities received from various locations of tissue will depend, for example, on the angle of incidence of the exciting beam as well as other parameters such as tissue wetness. Such unintended variations should be compensated in a device designed for screening purposes.

In one embodiment, a device may be brought into intimate contact with the tissue to collect responses from a large plurality of sites on the cervix without manipulation of the device. However, a device which directly contacts the cervix may cause other problems that interfere with the screening function. In particular, excessive pressure of the device on the cervix in an attempt to reduce tissue curvature can also exsanguinate the tissue, causing incorrect measurements. For this reason, non-contact devices that properly account for variations in fluorescence intensity would be preferred.

In the following discussions of the discrimination algorithms, normalized intensities $I_\lambda$ at various wavelength $\lambda_i$ will be used. To facilitate notations, $I_i$ will denote the normalized fluorescence responses of tissue at a wavelength $\lambda_i$.

For white light elastic backscatter spectroscopy, the instrument function, such as effects due to the detector response, source intensity, and the like should be eliminated from the data. For this purpose, a standard white target of 10% reflectance located outside the cervix is illuminated by the device over the spectral range of the white light measurement in exactly the same spatial scanning pattern as is done on the tissue. Ratios are formed by dividing the individual tissue spectra response recorded at each site on the cervix by the reference spectrum of the white target from the same scan position of the device. This eliminates the instrument response from each tissue spectrum and provides the first step in creating the final spectra from which the diagnoses of tissue can be made.

Furthermore, when recording backscattered responses to white light excitation of cervical tissue, the light source itself may differ between different instruments and may drift over time. This can influence detected signal intensities between instruments within a given instrument over time. It is thus advisable to perform a calibration with the white target just prior to each patient evaluation to minimize errors.

For white light elastic backscatter spectroscopy, the bandwidth of the detection electronics is typically substantially identical to the bandwidth of the illuminating beam. This may cause problems in final spectral normalization because stray light can inadvertently enter the detector. The stray light can be unwanted reflections from the illuminating portion of the device into the detection portion, or it can be "glint" from the surface of the cervix. Here, glint refers to the light reflected at the surface of the tissue without optically interacting with the tissue. Glint thus has the spectral characteristics of the light source, but does not contain information regarding the state of the tissue. Because both glint and the response from the white target contain the spectral content of the light source, the two spectra are identical to within a multiplicative constant.

The first step in normalization of the white light backscatter spectra is the elimination of any glint from the spectra. This type of signal in the data is known as Fresnel reflection, and occurs at boundaries where there is a change in the refractive index through which the optical radiation propagates. The index of refraction of moist tissue is known to be in the range of 1.33 to 1.37. Further understanding of the Fresnel reflection properties reveals that the amount of reflection occurring at the boundary will depend on the angle of incidence of the incoming radiation. A good approximation, then, is to assume the collected spectrum from a point on the tissue contains information regarding the tissue in the form of a spectral content $T(\lambda)$, and Fresnel reflection of unknown amount. If $S(\lambda)$ represents the total intensity of the white light backscattered from the tissue as a function of the wavelength $\lambda$ and $B(\lambda)$ represents the spectral response of the illuminated white target. Then $S(\lambda)$ can be written as:

$$S(\lambda)=T(\lambda)+\alpha B(\lambda), \tag{1}$$

where T(λ) is the desired spectrum without glint, and α is a scaling factor. The spectrum can be normalized in the form:

$$S(\lambda)/B(\lambda) = T(\lambda)/B(\lambda) + \alpha. \quad (2)$$

The scaling factor α can interfere with the diagnostic results obtained from the tissue and should therefore be either determined separately or if possible eliminated.

The scaling factor α can be eliminated in several ways. In one practice, if the optical signal response in the region from 410 nm to 420 nm is small, owing to the very large absorption caused by hemoglobin in the tissue, the minimum value of each spectrum can be set to zero in this region. This already eliminates a large portion of the offset, facilitating subsequent classification of the spectra by the algorithm described below.

Alternatively, the scaling factor α can be eliminated by processing the wavelength derivative of each spectrum.

Fluorescence spectra are recorded over a number of sites by UV excitation on the surface of the cervix, and then are normalized by the method described above. An exemplary excitation wavelength is 355 nm (wavelength-tripled Nd:YAG), but any other ultraviolet wavelength may be used. The spectra are normalized using eq. (2) and processed using an algorithm discussed below to classify the tissue type according to a specified screening requirement. The algorithm may be adjusted, for example, to screen for the presence of an advanced stage of the disease (CIN II/III). To adjust the algorithm, specific spectral training set data are fetched from, for example, the computer memory 24 and assembled into the suitable training sets. The training set data are collected with the same or with a similar device, with the state of the disease (or the absence of the disease) to be confirmed later through pathology. The training data can be stored in the analytical system as part of the algorithm, and can be read from memory and placed into categories depending on the screening requirement. For the above example, the CIN II/III training set data are placed in a first "abnormal" category, while the remaining spectra (normal, metaplasia, CIN I, etc.) are placed in a second "normal" category.

The purpose of the training set is to teach an analytical system those features in the spectra which would indicate an abnormal tissue state as opposed to a normal tissue.

In operation, the screening device is first "trained" to discriminate between normal and abnormal tissue using fluorescence. Depending on the type of screening required, the training data are called from memory and collected into normal and abnormal sets. Selected spectral regions are then extracted from each normalized training spectrum. It has been observed that the algorithm described below has an optimum tissue classification ability to differentiate between CIN II/III and other tissue states with an excitation wavelength of 355 nm and detection of fluorescence responses in the wavelength range of 414 nm to 450 nm and 451 nm to 489 nm. The spectral regions extracted for analysis may be different for different classification screening (e.g. for differentiating all CIN from normal tissue). After extracting the desired spectral subset of each specimen in the "training set", data points representing the intensity of the spectrum are plotted in an n-dimensional space where each axis represents a given wavelength. The dimensionality n is therefore equal to the number of distinct wavelengths. The data point for each test specimen j in the training set of n wavelength samples is thus described by a vector $I_j = (I_{j1}, \ldots I_{ji}, \ldots I_{jn})$.

It is known from the results of the respective biopsies on each test specimen in the training set which of these j specimens is classified as normal and which is classified as abnormal according to the desired classification screening. The spectra of the training set are grouped into two groups, j=(1, ... u) for all spectra to be considered as normal and j=(1, ... v) for all spectra of abnormal tissue, where u+v=n. The mean values $N_i = (I_{1i} + \ldots + I_{ji} + \ldots + I_{ui})/u$ are computed at each wavelength $\lambda_i$ for all the u spectra of the normal test specimens, where i spans over the n selected wavelengths $\lambda_i$. Similarly, the mean values $C_i = (I_{1i} + \ldots + I_{ji} + \ldots + I_{vi})/v$ are computed at each wavelength $\lambda_i$ for all the v spectra of the abnormal test specimens. This will result in two "points" in the n-dimensional space spanned by the n wavelengths $\{\lambda_1, \ldots \lambda_n\}$ wherein the average point corresponding to the normal tissue is described by the vector $N = (N_1, \ldots N_i, \ldots N_n)$, and the average point corresponding to the abnormal tissue in this n-dimensional space is $C = (C_1, \ldots C_i, \ldots C_n)$. These vectors are also referred to as "group mean vectors" and provide a measure against which unknown spectra obtained from cervixes are compared in order to classify such tissue as either normal or abnormal within a specified classification scheme.

Figure 8:
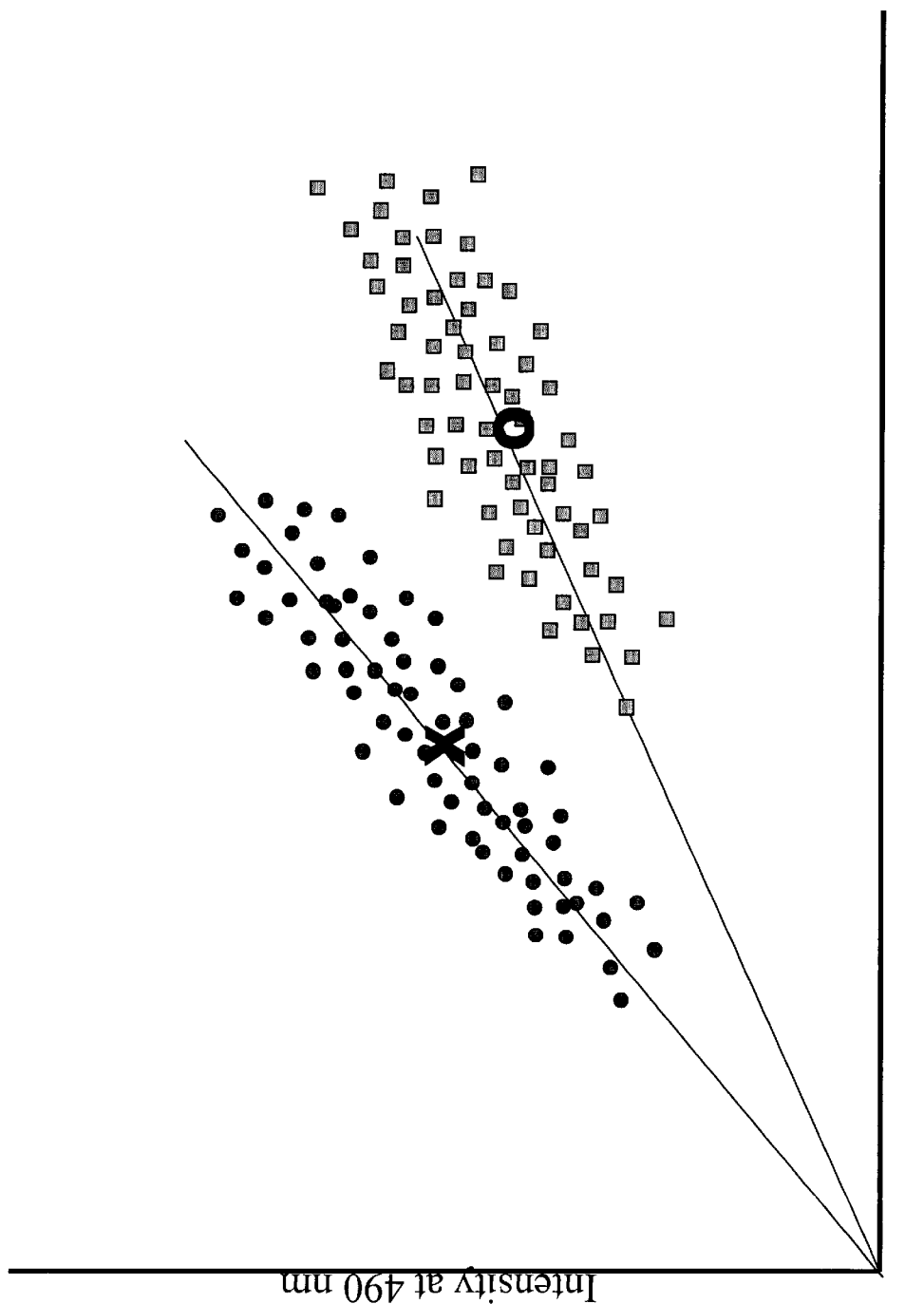
FIG. 8 shows a diagram of the normalized intensities $I_\lambda^{490\ nm}$ determined at a wavelength of 490 nm as a function of the normalized intensities $I_\lambda^{410\ nm}$ determined at a wavelength of 410 nm for normal tissue (NED) and abnormal tissue (CIN), respectively.

FIG. 8 shows a two-dimensional diagram of the normalized intensities $I_\lambda^{490\ nm}$ at a wavelength of 490 nm as a function of the normalized intensities $I_\lambda^{410\ nm}$ determined at a wavelength of 410 nm for normal tissue (NED) and abnormal tissue (CIN II/III), respectively. This simplified diagram is merely intended to be an instructive simplification of the actual process occurring in n-dimensional space, where n represents the total number of spectral intensities used in the classification. In this example, two intensities are selected and plotted. The spectra obtained from normal tissue appear to aggregate along a line with a slope which is greater than the slope obtained from spectra for abnormal tissue. This indicates that the ratio $I_\lambda^{490\ nm}/I_\lambda^{410\ nm}$ of the intensities at these wavelengths is equal to a first constant for normal tissue and equal to a second constant which is smaller than the first constant for abnormal tissue. The average value can be represented by a first point (denoted by "X") for the normal tissue and by a second point "O" for the abnormal tissue. For a more comprehensive analysis, more than two wavelengths can be represented as a surface in a multi-dimensional space, which will be discussed below.

A spectrum from an unknown tissue sample can be compared with the tissue types plotted in FIG. 8 by selecting the same two wavelength values and using the intensities at these wavelengths to plot the location of the unknown spectrum in this two-dimensional plot. A decision criterion must then be applied to determine to which tissue class the unknown tissue belongs. This criterion is a distance measure from the location of the point representing the spectrum in the two-dimensional space to each of the average locations. This distance, however, must account not only for "length" between the unknown spectral point and each of the average points, but also for the locations of the points relative to the scatter in the data. If, for example, the unknown tissue spectrum is plotted far from the NED average, but along the line of the scatter, it is considered to be "closer" to this class than if it were the same physical distance from the average point, but off the line. The criterion that takes account of the distance as well as the scatter characteristics in the data is the Mahalanobis distance calculation.

Highly reliable classification between two tissue types, then, is the result of large separation between the average points defining the regions of different tissue type, and relatively small scatter in the neighborhoods of these average points. Proper selection of spectral regions from the tissue spectra can maximize the separation between the two average points in the n-dimensional space. For example, when the intensities from 413 nm to 489 nm in the fluorescence spectra are used, the separation between the two average points in the n-dimensional space is over 13 units. Of course, the units on the distance depend on the units of the individual intensities at each wavelength in the spectra, which in turn depend on the method of normalization of the spectra. Therefore, it is no loss of generality to ignore the units of the computed distance as long as comparisons are always made within the same scale of units.

Random selections of spectra classified as NED against the CIN II/III class show a range of measured Mahalanobis distances to each average. For instance, for one spectrum, the distance to the average CIN II/III location was measured to be 15 units, but the distance to the NED average was less than 6 units. Clearly, this spectrum was identified as NED. In another example, the distance from a spectral point to the average of CIN II/III was measured as 8 units, much less than the distance between the two average points. However, the distance from the spectral point to the NED average was measured as only 4 units, indicating that the point belonged to the NED class.

When the distance between the two average points becomes small, the difference between the distances from a spectral point to both of these average points becomes small. When the difference is small, classification of an unknown spectrum becomes more difficult, because noise in the spectrum shifts the location of the spectral point slightly in the n-dimensional space. This decreases the sensitivity and specificity of the classification. As an example, the classification of CIN I vs. CIN II/III is only 51% sensitivity and 55% specificity. Looking at the Mahalanobis distances involved, the optimum distance between the two average points for the classification is only 1 unit, while the distances from typical spectra to each of these points is over 5.5 units. Furthermore, the difference between the distance from the unknown spectral point to the two averages is only 0.2 units to 0.3 units. This suggests that the two classes CIN I and CIN II/III are difficult to distinguish, resulting in poor sensitivity and specificity.

In its full complexity, the algorithm for determining whether a site on the cervix is abnormal or normal consists first of locating the positions representing the different tissue types for the screening in the n-dimensional space. This is done by evoking stored spectra or spectral characteristics from the computer. These stored responses are training data for the algorithm, and provide the information needed to locate the average response location for normal and abnormal tissue. They also provide the details on the scatter within typical data in order to determine distances relative to the preferred scattering in the data. The algorithm for determining whether a site on the cervix is abnormal or normal consists of first locating the n-dimensional point representing the fluorescence response from the selected site on the cervix. The algorithm computes the distances from this point to the average point of normal tissue and to the average point of abnormal tissue, with the average points computed as described above. The distances are typically computed in a non-Euclidian metrics as described below. Classification of the unknown point is completed by determining which distance is smaller, and including the unknown spectrum in that class.

The non-Euclidian metrics used is the Mahalanobis distance, sometimes also referred to as D-statistics. The Mahalanobis distance is used not to find the physical distance from one object to another, but to find the distance in terms of related characteristics and likelihood of occurrence of the two objects.

The Mahalanobis distance is obtained from the training set of the n wavelength samples represented by the vector $I_j = (I_{j1}, \ldots I_{ji}, \ldots I_{jn})$ described above. First, the group covariance matrices $G_N$ for those specimen in the training set that have been determined to be normal and the group covariance matrices $G_C$ for those specimen in the training set that have been determined to be abnormal are computed as follows:

$$G_N = \frac{1}{u-1}(I_u - N)^T(I_u - N) \quad \text{and} \qquad 3$$

$$G_C = \frac{1}{v-1}(I_v - C)^T(I_v - C), \qquad 4$$

where u and v are the number of specimens in the normal and abnormal sets respectively, $I_v$ and $I_u$ are the respective matrices of all the normalized intensities, and N and C are group mean matrices for normal and abnormal training sets, respectively. The group mean matrices consist of u vectors N and v vectors C for the respective two groups. It follows from the above, that $I_u$ for normal tissue is a u×n matrix and a $I_v$ for abnormal tissue is a v×n matrix. The $G_N$ and $G_C$ matrices are both n×n matrices, wherein n represents the total number of wavelengths sampled in the response spectra.

A "pooled within-group" covariance matrix G can be defined as the weighed average of the two group covariance matrices, $G_N$ and $G_C$:

$$G = \frac{1}{n-1}((u-1)G_N + (v-1)G_C) \qquad 5$$

The Mahalanobis distances, d(S,N) and d(S,C) of an unknown, or unclassified normalized spectrum, $S(\lambda_i)=S$ in the n-dimensional space from the group mean vectors, $N(\lambda_i)=N$ and $C(\lambda_i)=C$, respectively, can then be computed as follows:

$$d(S, N) = \sqrt{|(S-N)^T \cdot G^{-1} \cdot (S-N)|} \quad \text{and} \qquad 6$$

$$d(S, C) = \sqrt{|(S-C)^T \cdot G^{-1} \cdot (S-C)|} \qquad 7$$

Thus, target tissue in the cervix can be classified using the aforedescribed Mahalanobis distance metrics based on a vector S of measured fluorescence optical responses and test specimens in the normal and abnormal sets. If d(S,N)>d(S,C), the target tissue will be classified as CIN (positive), whereas the target tissue is classified as NED (negative) if d(S,N)<d(S,C).

According to another embodiment of the present invention, Quadratic Discriminant Analysis (QDA) is used to compute the Mahalanobis distances of the point S to the respective group mean vectors N and C. The classification scores $cf_N(S)$ and $cf_C(S)$ of the Mahalanobis distances as previously determined are here corrected by adding a term which includes the natural logarithm of the determinant of the respective group covariance matrices $G_N$ and $G_C$, as shown in equations 8 and 9:

$$cf_N(S) = \sqrt{|(S-N) \cdot G_N^{-1} \cdot (S-N)^T|} + \ln(|det(G_N)|) \qquad 8$$

-continued $$cf_C(S) = \sqrt{|(S-C) \cdot G_N^{-1} \cdot (S-C)^T|} + \ln(|det(G_C)|) \quad 9$$

As described above with reference to the first embodiment, the tissue is classified as negative if $cf_N(S) < cf_C(S)$, whereas the tissue is classified as positive if $cf_C(S) < cf_N(S)$.

Under some circumstances, the "pooled within-group" covariance matrix, G, or either of the group covariance matrices, $G_N$ and $G_C$, may be singular, so that the respective inverse matrices $G^{-1}$, $G_N^{-1}$ and $G_C^{-1}$ are undefined and the Mahalanobis distances cannot be computed using the equations 6, 7, 8 and 9.

This situation can be alleviated by using a Regularized Discriminant Analysis (RDA), wherein a weighted combination of the "pooled within-group" covariance matrix G and the respective group covariance matrices, $G_N$ and $G_C$, is used to evaluate the Mahalanobis distances of the point S representing spectra from an unclassified tissue sample to the respective group mean vectors N and C of the respective NED and CIN classes. For this purpose, respective Friedman matrices $\Omega_N(\beta,\gamma)$ and $\Omega_C(\beta,\gamma)$ are defined as follows:

$$\Omega_N(\beta, \gamma) = (1-\gamma)[(1-\beta)*G_N + \beta*G] + \frac{\gamma}{n}*tr((1-\beta)*G_N + \beta*G)*I \quad 10$$

and $$\Omega_C(\beta, \gamma) = (1-\gamma)[(1-\beta)*G_C + \beta*G] + \frac{\gamma}{n}*tr((1-\beta)*G_C + \beta*G)*I \quad 11$$

where "tr" is the matrix trace operator representing the sum of the diagonal elements of the matrix, and I is the n×n unity matrix, where n is the total number of wavelengths representing spectral responses.

Modified Mahalanobis distances of an unknown or unclassified spectrum S from the group mean vectors N and C, which are equivalent to the classification scores $cf_n(S)$ and $cf_C(S)$, can then be computed using the Friedman matrices $\Omega_N(\beta,\gamma)$ and $\Omega_C(\beta,\gamma)$ of equations (10) and (11) in a manner similar to that of equations (6) and (7):

$$cf_N(S) = \sqrt{|(S-N) \cdot \Omega(\gamma, \beta)^{-1} \cdot (S-N)^T|} \quad \text{and} \quad 12$$

$$cf_C(S) = \sqrt{|(S-C) \cdot \Omega(\gamma, \beta)^{-1} \cdot (S-C)^T|} \quad 13$$

As before, the tissue of the cervix is normal (negative) if $cf_N(S) < cf_C(S)$, and abnormal (positive) if $cf_N(S) > cf_C(S)$.

The weighting parameters β and γ are determined experimentally during the calibration of the probe at the factory.

The probe can be shipped pre-calibrated, with calibration parameters embedded in the processor 12 or stored in a (removable) memory 24. The only calibration carried out in the field involves an automated calibration of the white light source using a white, spectrally flat reflector.

It has been experimentally observed that LIF spectra of excited with a wavelength of 355 nm can predict the presence of CIN II/III as the abnormal tissue class in the presence of NED tissue with a sensitivity of over 91% and a specificity of approximately 92% using the Regularized Discriminant Analysis (RDA) of eqs. (12) and (13). This performance is far superior to the pap smear screening. However, when many sites over the cervix are being interrogated, even this level of performance can lead to erroneous readings at some sites.

If 100 points are interrogated on the surface of the cervix, and if the probability for an error in the diagnosis at any one point is 10%, then the probability that the entire scan will be without error is only $2.66 \times 10^{-5}$. Decreasing the probability of error to 5% reduces the probability of an error-free scan to only $5.9 \times 10^{-3}$, and with a 1% error probability per point, the probability for an error free scan is 0.37. Methods to decrease the error rate are important in screening devices.

The reliability of the diagnosis can be improved by measuring the tissue response to additional excitation wavelengths. For example, a white light elastic backscatter capability can be added to the screening device. This capability augments the fluorescence capability (LIF) discussed above.

White light elastic backscatter spectra are generated when the light from a broadband source, such as a xenon lamp, impinges on the sample and interacts with the sample by diffused reflectance. The diffusely scattered light from the surface is collected and decomposed into its spectral components. When cervical tissue is interrogated by this method, information regarding the amount of vascularization and the amount of optical scattering can be extracted from the spectra.

An algorithm similar in operation to the algorithm for fluorescence can make screening determinations of tissue status with the white light elastic backscatter spectra. First, however, the spectra must be properly normalized, and influences of stray light and glint must be eliminated from each spectrum. As mentioned earlier, the stray light causes a constant offset of the spectrum from the baseline.

As mentioned above, the findings of the optical screening method should be confirmed by subsequent pathologic examination the target tissue that was optically inspected. The determination of the NED and CIN group mean vectors N and C respectively was carried out by using a conventional colpoprobe as described, for example, in U.S. Pat. No. 5,813,987, on a large number of target tissues, all of which were subsequently classified by pathologic examination of excised tissue from the exact locations where the optical responses were taken.

The algorithm used to classify the white light elastic backscatter spectra is identical in operation to the algorithm for fluorescence. The only difference in the execution of the algorithm is the nature of the normalization of the spectra and the subset of spectral regions used in the Mahalanobis distance calculation. As mentioned above, first the offset α should be eliminated from the spectra. Then, for example, three wavelength regions are selected. We have found that the regions 401 nm to 447 nm, 448 nm to 495 nm, and 542 nm to 589 nm are suitable for classifying tissue conditions from the white light backscatter data. For each spectrum, these spectral regions are extracted from the total spectrum and the total (integrated) area under the curves is computed. Each data point of the extracted subset is then divided by the total area to create a final normalized set of data from the original spectrum.

The algorithm uses the stored spectra as training data to identify the proper group mean averages for the screening. The algorithm is applied to each tissue spectrum collected by white light elastic backscatter and an association with a defined class is made based on the Mahalanobis distance criterion according to the equations (6) to (13).

Suitable weighting parameters β and γ for the RDA algorithm of equations (12) and (13) can be determined, for example, by randomly selecting approximately 60% of the spectral values (and their associated pathologic classifications) as a "training" spectrum and classifying the balance of the spectral values as "unclassified" spectrum S using the equations (12) and (13). This process was repeated in an iterative manner until optimal weighting parameters were determined. These weighting parameters, together with the best group mean vectors N and C are then set as constant parameters in each screening device. It should be appreciated that the classification into positive and negative classes depends on the determination of the threshold between the classes.

The aforementioned spectral ranges of 401 to 447 nm, 448 to 495 nm and 542 to 589 nm were selected to classify pathological tissue conditions based on the backscattered white light from target tissue. In one practice, only NED was classified as negative tissue and only CIN II–III was classified as positive tissue. Respectively. With this classification, the RDA algorithm yields a sensitivity of 93% and a specificity of 89%.

In another practice, CIN I (the lowest grade of cervical intraepithelial cancer) was included in the NED class, using the same algorithm. In this case, group mean vectors N and C were modified to reflect the inclusion of the CIN I tissue samples in the training set in the group mean vector N rather than in the group mean vector C. With this classification, the RDA algorithm yields a sensitivity of 93% and specificity of 90%.

In still another practice, CIN I as well as all more severe forms of CIN (grades I/II and above) were included in the positive class. In this case, group mean vectors N and C were modified to reflect the inclusion of the CIN I tissue samples in the training set in the group mean vector C rather than in the group mean vector N. With this classification, the RDA algorithm yields a sensitivity of 87% and specificity of 86%.

In the above examples, the tissue samples were analyzed using the Mahalanobis distances derived from eqs. (12) and (13). The particular parameter values are listed in Table 1. It should be pointed out that the boundary which differentiates between the respective NED class (which may or may not include the CIN I tissue sample) and the CIN class is an n-dimensional surface in the n-dimensional space spanned by the n selected wavelengths $\lambda_1, \ldots, \lambda_n$, as described above. Computing the Mahalanobis distance between a spectrum obtained for a tissue sample to be examined and a reference spectrum is therefore different from forming ratios of spectral responses obtained with different wavelength pairs, as is common in the prior art. When confronted with a large number, for example ten or more, ratios of fluorescence responses for a tissue sample, there is no obvious a priori criterion for establishing a meaningful weighting algorithm, i.e., for discerning which of these ratios is more important for discriminating between healthy and diseased tissue. Moreover, whereas tissue discrimination may be more successful with other cancers, such as colon cancer where strong visual markers are present and observable, there is no apparent visual marker of pre-cancer in the cervix.

According to another embodiment of the present invention, both white light backscattering and LIF responses are measured, with the responses taken from identical sites in the target cervix.

Figure 10:
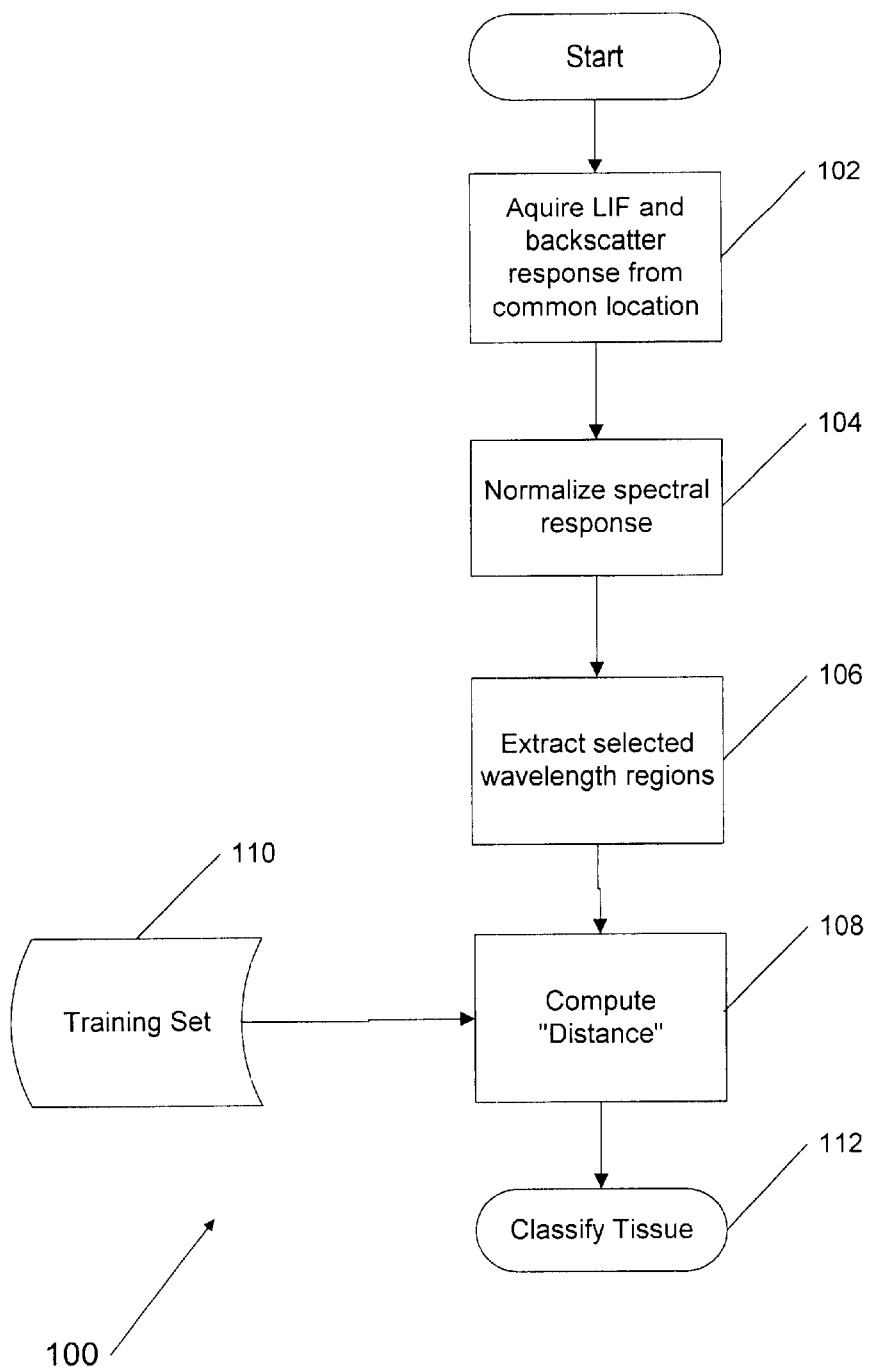
FIG. 10 is a process flow for tissue classification according to a first embodiment of the invention.

Referring now to FIG. 10, an exemplary process 100 for classifying cervical tissue combines the fluorescence and white light data into a single decision algorithm. In step 102, the fluorescence spectrum (LIF) and the white light backscatter spectrum are collected from a common location on the cervix. Each spectrum may then be normalized, for example, to the integrated spectral area, as described previously, step 104. Selected wavelength regions are extracted from each spectrum and combined to form an ordered data set which includes both the fluorescence intensities and the white light intensities, step 106. The boundary between NED tissue and CIN tissue is determined by computing in an n-dimensional space a statistically significant "distance", such as the Mahalanobis distance, step 108, using training data 110 obtained with fluorescence and white light data. The cervical tissue is classified based on the Mahalanobis distances, as discussed above, step 112.

Alternatively or in addition, the fluorescence spectrum and the white light spectrum from a specific location on the cervix may be processed before being classified, for example, by dividing the fluorescence spectrum by the white light spectrum, thus producing a residual or intrinsic fluorescence spectrum. Or the fluorescence spectrum may be multiplied by or convoluted with the white light spectrum, thereby combining the classification ability of the two different spectra into a single spectrum.

Figure 11:
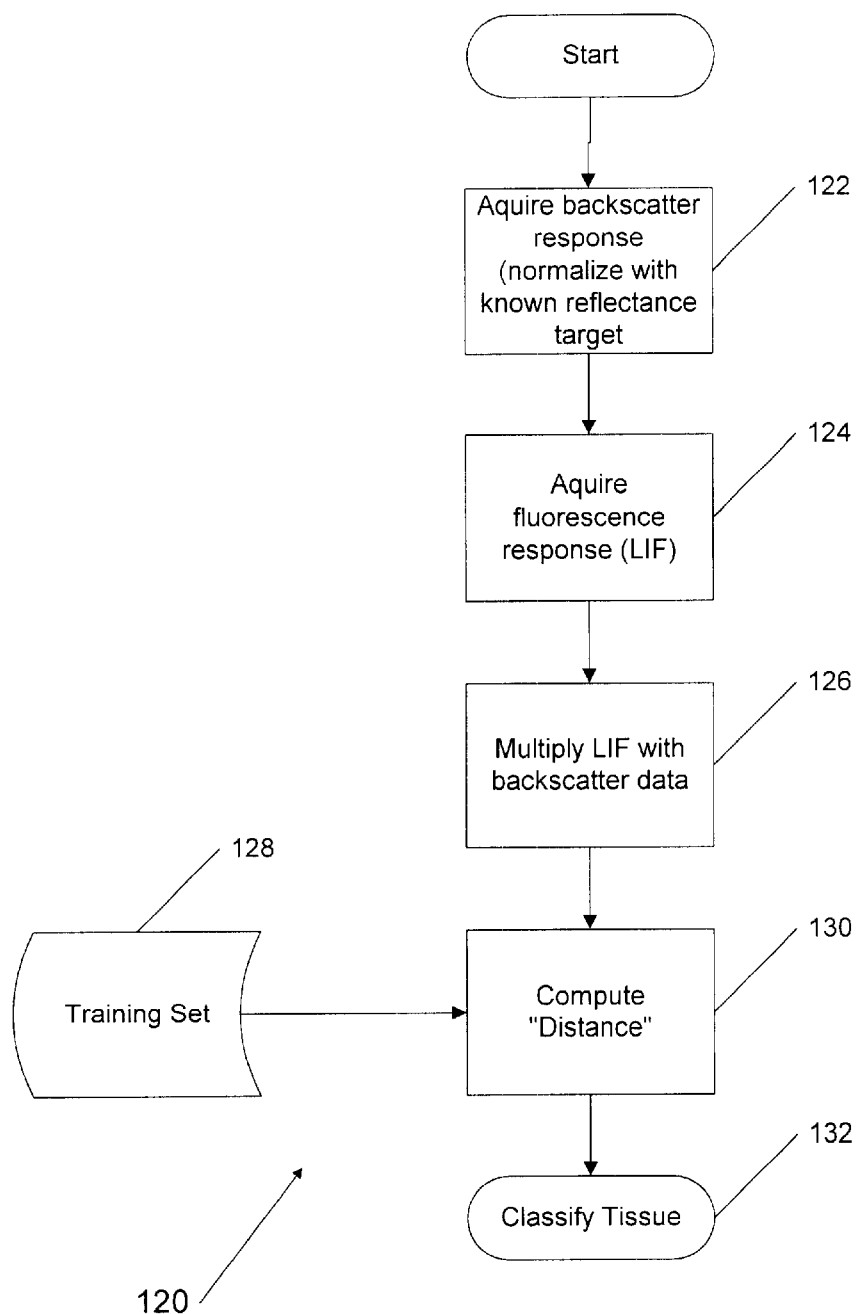
FIG. 11 is a process flow for tissue classification according to a second embodiment of the invention.

Referring now to FIG. 11, in another process 120 of combining the data from fluorescence and white light backscatter, a ratio of the white light backscatter response data to the 10% reflecting target is formed, step 122. Fluorescence response data are generated from the same location on the tissue, step 124, and the resulting spectrum is convoluted, for example, multiplied with each other, step 126. This operation enhances the spectral features of the resulting fluorescence spectrum. The boundary between NED tissue and CIN tissue is determined by computing in an n-dimensional space, for example, the Mahalanobis distance, step 130, using previously determined training data 128. The cervical tissue is classified based on the Mahalanobis distances, as discussed above, step 132. Algorithmic classification of these combined spectra was 90% sensitivity and 83% specificity.

The algorithms described above therefore include in their respective group mean vectors N and C data from both LIF and backscattered white light type spectra. It should be noted that the absolute intensity of LIF responses is much smaller than that of the backscattered white light, and that the two sets should therefore be normalized to approximately the same average intensity.

Whereas the spectral response can be normalized at specific wavelengths (for example, 355 nm for LIF and 480 nm for white light backscattering), other normalization schemes involving, for example, integrating the total response over the measured spectral range, can be used as well, and the present invention is not limited in any way by the specific normalization scheme employed.

In typical cervix screening applications, a plurality of sites within the target cervix is examined. For example, 100 or more individual sites may be individually excited by either a Uv beam or with white light, or with a combination of these excitation sources.

Figure 12:
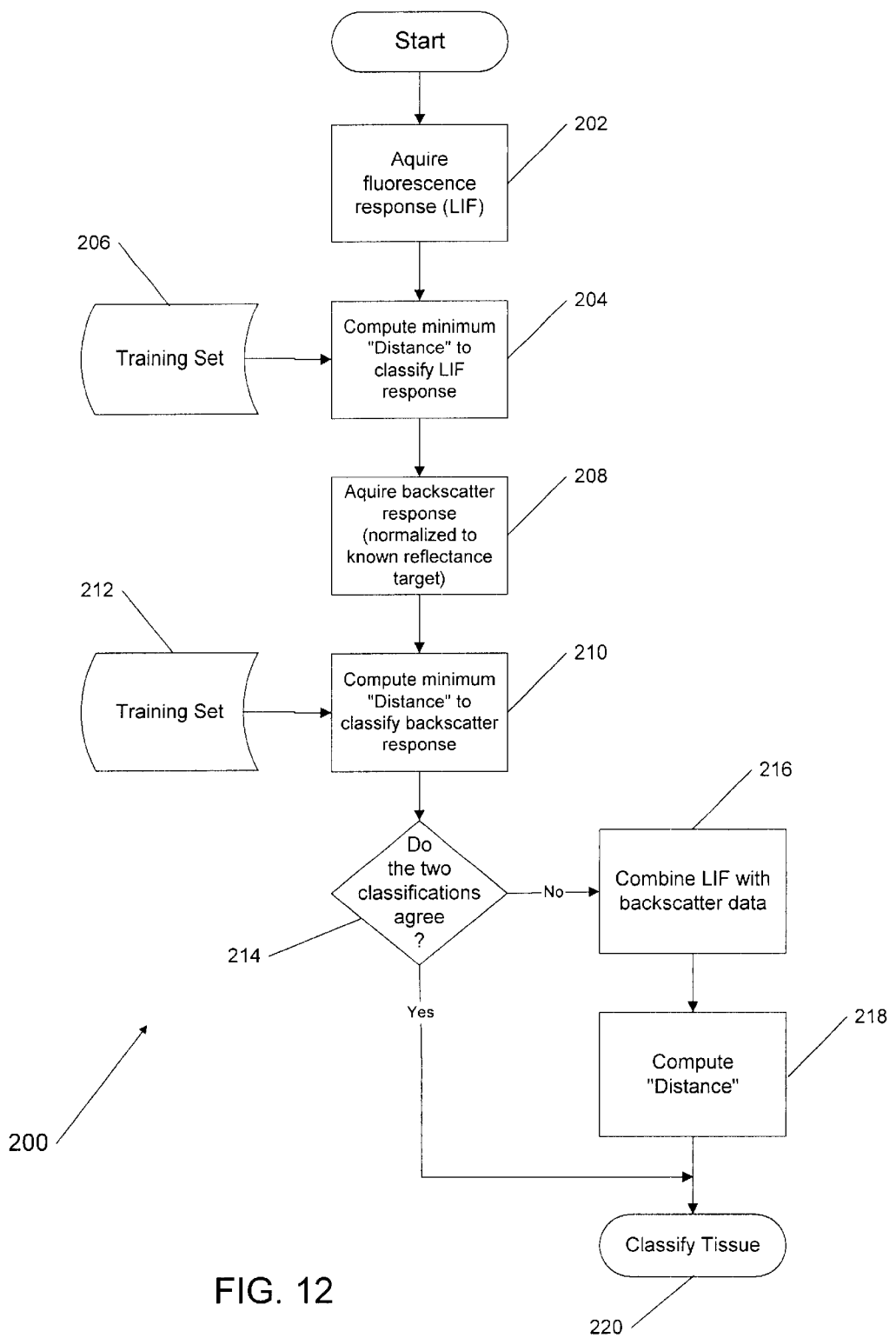
FIG. 12 is a process flow for tissue classification according to a third embodiment of the invention.

As seen from the experimental results discussed above, the specificity of the results can be less than 100%. As a result, a cervix may be erroneously classified as positive in a screening examination if just a single site from the 100+ sites probed was found to be positive. It would therefore be desirable have multiple opportunities for classifying a particular region of tissue. Referring now to FIG. 12, in yet another process 200 of combining the data from fluorescence and white light backscatter, the fluorescence response (LIF) is acquired from the tissue region, step 202, and the tissue is classified using the Mahalanobis distance algorithm into, for example, NED vs. all CIN, step 204, using the training set 206. The white light backscatter spectrum, which may be normalized to a target of known reflectivity, is acquired, step 208, and the tested with the aforedescribed Mahalanobis algorithm for the same classification, step 210, using the training set 212. If the two results agree, step 214, the classification is terminated with that result, step 220. If the two classifications disagree in step 214, a third classification is performed using the combined spectral information, step 216, to compute a "blended" Mahalanobis distance, step 218, and provide the final classification, step 220. Using this method, classification of NED vs. all CIN can be 90% sensitive and 90% specific.

Although this level of performance is far superior to the pap smear screening, it offers the opportunity for error. We have found that is possible to include a spatial discrimination algorithm in the analysis to ensure that at least two neighboring sites return a positive classifications before the target cervix is classified as positive for CIN. This technique of spatial comparison eliminates the occasional random error at a single point, but reduces the spatial resolution of the device. Because the design of the scanning pattern is such that the spacing of interrogation points is smaller than the typical pre-cancerous lesion (approximately 2 mm in diameter), this loss of spatial resolution is not a problem in this embodiment.

Figure 9:
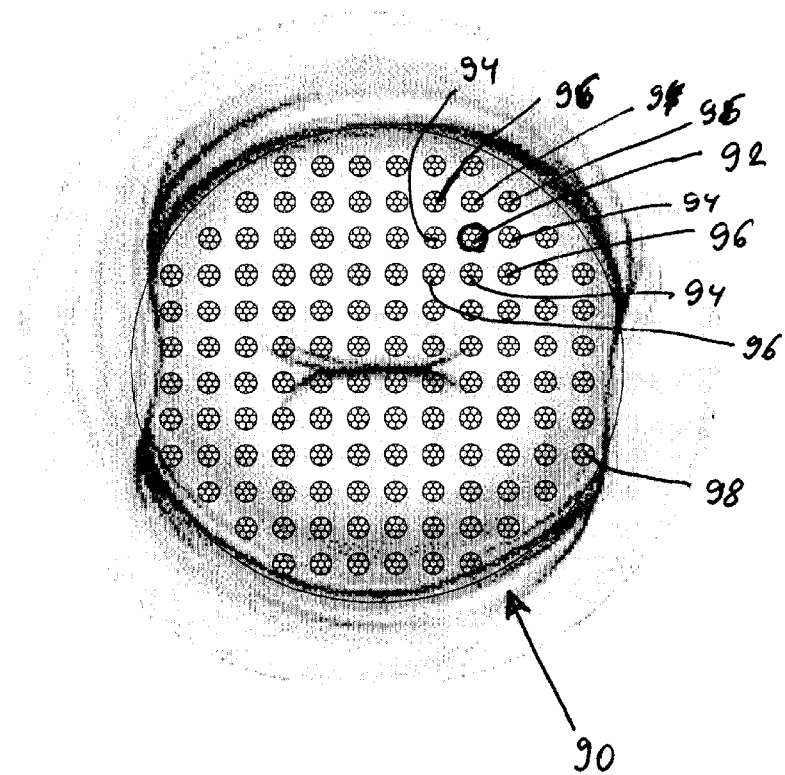
FIG. 9 shows interrogation sites on a cervix.

Referring now to FIG. 9, in one embodiment of the spatial discrimination algorithm, the sites probed may be arranged in a predetermined pattern for example, in the form of an array 90. As seen from FIG. 9, the array need not be square or rectangular and may have any pattern with a predetermined arrangement of tissue sites to be probed. A rectangular array may have pxq sites, for example, 10 rows and 12 columns when probing a total of 120 sites on the cervix. An exemplary array S having elements $S_{k,1}$ denotes the spectral response from each tissue site wherein the index k may span the range from 1 to p and the index l may span the range from 1 to q. With this notation, all spectral responses $S_{k\pm1,l\pm1}$, will be from sites 94, 96 that are "nearest neighbor" to the "central" site 92 represented by the spectral responses $S_{k,1}$. The number of neighboring sites can be as high as 8 and as low as 2 (for corner sites 98 of the array). A cervix may then be classified as positive if at least one spectral response $S_{k,1}$ is classified as positive and at least one additional spectral response $S_{k\pm1,l\pm1}$ is also classified as positive by the same algorithm.

In yet another embodiment of the spatial discrimination algorithm, the cervix may be scanned along a spiral path (not shown). Each spectral responses $S_k$ can be represented by a single index, k, with k being the number of steps from an origin. A cervix may be classified as positive if at least one spectral responses $S_k$ is classified as positive and at least one additional spectral responses $S_{k\pm1}$ is also classified as positive. In each of the aforedescribed embodiments, an automated scanner, as described with reference to FIG. 1, can be used to drive an optical assembly in a step-wise fashion, obtaining responses spaced, for example, approximately 1 mm apart.

Each site probed can be displayed on a map of the cervix, as illustrated in FIG. 9, identifying the location of those sections of the cervix which are found to be positive. This facilitates greatly the selection of sites from which subsequent biopsies may be taken.

The classification of target tissue into classes such as NED and CIN depend both on the definition of the classes and the group mean matrices N and C for these classes, as discussed above. The calibration of a screening system and is ability to discriminate between target tissues, even after units have been delivered to the field, may be improved by increasing the number of samples in the training set and by updating calibration data. One method of maintaining the calibration and updating may consist of having highly qualified colposcopists provide the manufacturer with both experimentally obtained spectral responses and related pathology results from substantially the same tissue. For example, a removable memory medium 26 shown in FIG. 1 may be included for collecting such data. Alternatively, such data may be entered online or via a network connection.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

| Measurement Type | Tissue Classification | Sensitivity | Specificity | Spectral Regions |
|---|---|---|---|---|
| Fluorescence | NED vs.CIN II/III | 91% | 93% | [413, 451] & [452, 489] |
| Fluorescence | NED + CIN I vs. CIN II/III | 87% | 87% | [413, 451] & [452, 489] |
| Fluorescence | NED vs. CIN I/II/III | 90% | 87% | [413, 451] & [452, 489] |
| White Light Backscatter | NED vs. CIN II/III | 86% | 73% | [401, 447], [448, 495], & [542, 589] |
| White Light Backscatter | NED+ CIN I vs. CIN II/III | 85% | 72% | [401, 447], [448, 495], & [542, 589] |
| White Light Backscatter | NED vs. CIN I/II/III | 86% | 70% | [401, 447], [448, 495], & [542, 589] |

What is claimed is:

1. A diagnostic system for optically classifying cervical tissue into pathological classes, the system comprising:
   a) an optical radiation source for inducing a response signal in a cervical tissue, the radiation source comprising:
      i) a UV light source that induces a fluorescence response in cervical tissue; and,
      ii) a broad spectrum light source that induces a backscatter response in cervical tissue;
   b) a detector for detecting the response signal, the detector comprising a first system for detecting the fluorescence response and a second system for detecting the backscatter response; and,
   c) a processor that compares the response signal with a reference signal by computing a distance between the response signal and the reference signal;
   wherein at least one of the fluorescence response and backscatter response is scaled with respect to the other of the backscatter response and fluorescence response, and wherein the reference signal is obtained from a cervical tissue sample of known pathology, and the distance between the response signal and the reference signal is used to classify the cervical tissue.

2. The diagnostic system of claim 1, wherein said distance is a Mahalanobis distance.

3. The diagnostic system of claim 1, wherein at least one of said optical radiation source and said detector are spaced apart from said cervical tissue.

4. The diagnostic system of claim 1, wherein said UV light source is a laser.

5. The diagnostic system of claim 4, wherein said laser is selected from the group consisting of a frequency-tripled Nd:YAG laser, a nitrogen laser and He—Cd laser.

6. The diagnostic system of claim 1, wherein said optical radiation source is a light source emitting in the visible/infrared spectral range.

7. The diagnostic system of claim 6, wherein said light source is a xenon lamp.

8. The diagnostic system of claim 1, wherein said response signal is a normalized signal.

9. The diagnostic system of claim 1, wherein said source of optical radiation comprises a first light source that emits ultraviolet light and a second light source that emits broad spectrum light.

10. The diagnostic system of claim 1, wherein said detector comprises at least two detection systems, at least one of which detects said fluorescence response and at least one of which detects said backscatter response.

11. A method of optically classifying cervical tissue into pathological classes, the method comprising the steps of:

Exciting cervical tissue with optical radiation and inducing at least one of a fluorescence and backscatter response in said cervical tissue, wherein at least one of the fluorescence response and backscatter response is scaled with respect to the other of the backscatter response and fluorescence response, Detecting said backscatter or fluorescence response and producing a response signal, Comparing said response signal with a reference signal obtained from cervical tissue of known pathological condition and which is grouped into at least two pathological classes, Computing a distance between said response signal and said reference signal, and Assigning said cervical tissue to a pathological class based upon a response signal producing the smallest distance.

12. The method of claim 11, wherein said distance is a Mahalanobis distance.

13. The method of claim 11, wherein said optical radiation is ultraviolet light.

14. The method of claim 11, wherein said comparing step comprises the step of normalizing said response signal.

15. A method of optically classifying cervical tissue into pathological classes, comprising: exciting the cervical tissue with optical radiation and detecting a fluorescence response in the cervical tissue, comparing the fluorescence response with a fluorescence reference response obtained from cervical tissue samples of known pathology and grouped into at least two pathological classes by computing a first distance between the fluorescence response and the reference response and assigning the cervical tissue to the class which produces the response signal having the smallest first distance, detecting a backscatter response from the cervical tissue, comparing the backscatter response with a backscatter reference response obtained from cervical tissue samples of known pathology and grouped into the at least two pathological classes by computing a second distance between the backscatter response and the backscatter reference response and assigning the cervical tissue to the class which produces the backscatter response signal having the smallest second distance, and if the class of the cervical tissue based on the first distance is identical to the class of the cervical tissue based on the second distance, classifying the cervical tissue into the class representing the first and second distance, and if the class of the cervical tissue based on the first distance is different from the class of the cervical tissue based on the second distance, combining fluorescence response with the backscatter response and computing a third distance between the combined response and a respective combined fluorescence and backscatter reference response and assigning the cervical tissue to the class which produces the combined response signal having the smallest third distance.

* * * * *